United States Patent [19]
Lafon

[11] 3,959,283
[45] May 25, 1976

[54] AMINO-DERIVATIVES OF 1,4-BENZODIOXAN

[75] Inventor: Louis Lafon, Paris, France

[73] Assignee: Laboratoire L. Lafon, Maisons-Alfort, France

[22] Filed: Jan. 17, 1975

[21] Appl. No.: 542,023

Related U.S. Application Data

[63] Continuation-in-part of Ser. No. 408,947, Oct. 23, 1973.

[30] Foreign Application Priority Data

Jan. 25, 1974  United Kingdom.............. 3547/74

[52] U.S. Cl.......................... 260/268 BC; 424/250
[51] Int. Cl.².............. C07D 295/10; A61K 31/495; C07D 405/06
[58] Field of Search .............. 260/268 BC; 424/250

[56] References Cited
OTHER PUBLICATIONS

Mndzhoyan, A. L. et al., C.A. Vol. 70, p. 96754t, (1969).

Primary Examiner—Alton D. Rollins
Assistant Examiner—Jose Tovar

[57] ABSTRACT

1-[2-(1,4-Benzodioxanyl)methyl]-4-(2-hydroxyethyl)-piperazine hemifumarate and the related compounds of formula:

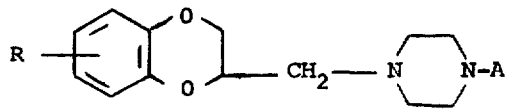

in which R is hydrogen or alkyl; and A is —CH(CH$_3$)COOC$_2$H$_5$, —CH$_2$CH$_2$O(C$_6$H$_4$) (CH$_3$)$_2$, —CH$_2$CH(OH)Ph or —CH$_2$CO(C$_6$H$_3$) (OCH$_3$)$_3$ or A is —Z—OR$_1$, —CH$_2$CHOR''$_1$CH$_2$OR'$_1$, —Z—CO—B or amidino, where Z is a linear or branched divalent hydrocarbon chain of 1 to 3 carbon atoms, R'$_1$ and R''$_1$, which may be indentical or different, are each hydrogen, alkyl, or acyl, B is OH, alkoxy, or a secondary, tertiary or N-heterocyclic amino radical, and R$_1$ is alkyl, acyl other than nicotinoyl or 3,4,5-trimethoxybenzoyl, or, when R is other than hydrogen, hydrogen, and its acid addition salts, are useful in therapy as vasodilators and α-blocking agents.

6 Claims, No Drawings

AMINO-DERIVATIVES OF 1,4-BENZODIOXAN

This application is a continuation-in-part to my United States Application Ser. No. 408947, filed Oct. 23rd, 1973.

This invention relates to new amino derivatives of 1,4-benzodioxan.

Compounds belonging to N-[2-(1,4-benzodioxanyl)-methyl]-piperazine family are known. It is apparent especially from the investigation of the products described by Toldy et al in Acta Chimica Academiae Scientiarum Hungaricae, 1966, 49, 265, by Swain in United States Patent Specification No. 2,695,295 and by Archer in United States Patent Specification No. 3,362,956, that there is no therapeutic property common to all members of this family. Most of the compounds are either inactive, or too toxic when administered orally, or are devoid of a blocking effect with respect to adrenergic receptors when injected.

The new amino derivatives of 1,4-benzodioxans do not possess the defects of the prior art; these new derivatives are:

a. 1-[2-(1,4-Benzodioxanyl)-methyl]-4-(2-hydroxyethyl)-piperazine hemifumarate; and
b. the compounds of general formula:

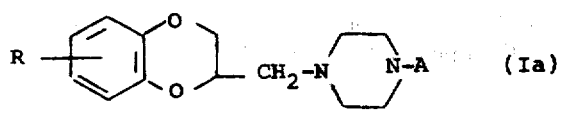

in which R is hydrogen or alkyl and A is —CH(CH$_3$)COOC$_2$H$_5$,

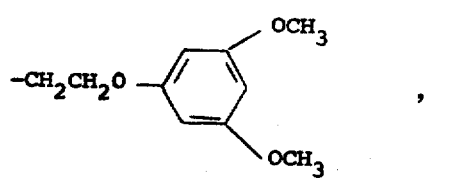

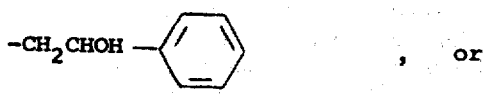

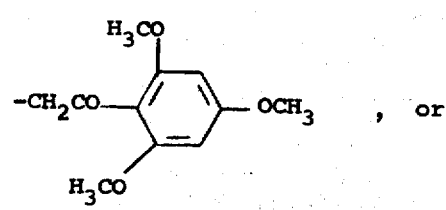

A is —Z—OR$_1$, —CH$_2$CHOR''$_1$CH$_2$OR'$_1$, —Z—CO—B or amidino, where Z is a linear or branched divalent hydrocarbon chain of 1 to 3 carbon atoms, R'$_1$ and R''$_1$, which may be identical or different, are each hydrogen, alkyl, or acyl, B is OH, alkoxy, or a secondary, tertiary or N-heterocyclic amino radical, and R$_1$ is alkyl, acyl (other than nicotinoyl or 3,4,5-tri-methoxybenzoyl), or, when R is other than hydrogen, hydrogen, or an acid addition salt thereof.

By amidino group is to be understood a group possessing the structure —C(NH$_2$):NH optionally substituted on one or both nitrogens, or a group of formula:

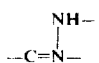

included in a ring. Examples of such cyclic amidino groups are 2-imidazolyl, 2-pyrimidinyl, 2-$\Delta^2$-imidazolidinyl and 2-(1,4,5,6-tetrahydropyrimidinyl).

Suitable compounds, in addition to 1-[2-(1,4-benzodioxanyl)-methyl]-4-(2-hydroxyethyl-)piperazine hemifumarate, include the compounds of the formula:

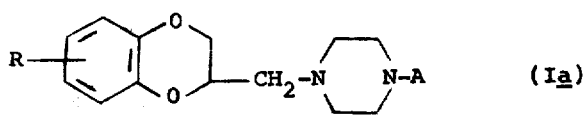

in which R is hydrogen or alkyl of 1 to 5 carbon atoms, and A is —CH$_2$CH$_2$OR$_1$, —CH$_2$CHOR''$_1$CHOR'$_1$, 2-pyrimidinyl or —CH$_2$COB where R'$_1$ and R''$_1$, which may be identical or different, are each hydrogen, alkyl of 1 to 5 carbon atoms, alkanoyl of 1 to 5 carbon atoms, R$_1$ is alkyl of 1 to 5 carbon atoms, alkanoyl of 1 to 5 carbon atoms, or when R is other than hydrogen, hydrogen, and B is a secondary, tertiary or N-heterocyclic amino radical, e.g. 2,6-dimethyl anilino-; and their acid addition salts.

The compounds of the invention may be made by reacting, preferably in a solvent at the reflux temperature of the solvent, a N-[2-(1,4-benzodioxanyl)-methyl]-piperazine of general formula (II)

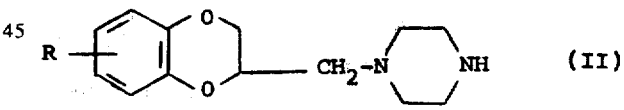

with a halide of general formula

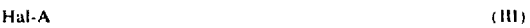

wherein Hal is halogen (preferably chlorine or bromine), and R and A are as hereinbefore defined, or, when a compound of general formula (I) wherein A is —CH$_2$CH(OH)Ph is desired, with an epoxide of general formula (IV)

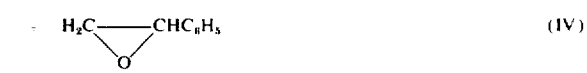

or by reacting, preferably in a solvent at the reflux temperature of the solvent, a 1,4-benzodioxan derivative of general formula (V)

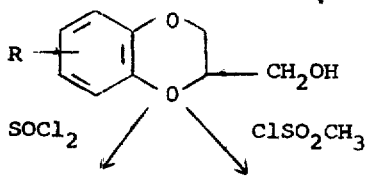

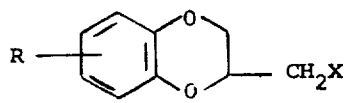

in which X is halogen or methanesulphonyloxy and R is as hereinbefore defined, with a compound of formula (VI)

wherein A is as hereinbefore defined, and optionally converting a base so obtained into an acid addition salt thereof.

The compound of general formula (II) can be prepared by reacting a 1,4-benzodioxan derivative of general formula (V) with piperazine.

The reaction between compounds (II) and (III) is suitably carried out in an inert solvent at a temperature of 15°C to the reflux temperature of the solvent, by reacting one mol of compound (II) with at least one mol of compound (III). In Examples 10 to 13 given below, the solvent used is dimethylformamide (DMF) and an excess of compound (III) over compound (II) is employed.

One or other of these processes can be chosen depending on the instability of the functional groups present in the radical A.

Compounds wherein A contains an ester group can be formed, for example, from a compound in which A contains a hydroxy group by known methods of esterification, e.g. by reaction with an acid chloride or an acid anhydride.

The solvents used in the reactions indicated above are preferably anhydrous solvents, for example tetrahydrofuran, dimethylformamide, benzene, toluene, xylene, a lower alcohol, or a mixture of such solvents.

There can be some uncertainty, when R is alkyl, as to the position of the group R.

The acid addition salts of the compounds of the invention ae produced by bringing the bases into contact with an appropriate inorganic or organic acid.

The compounds of formula II can be formed from pyrocatechol or one of its derivatives of formula VI in accordance with the following scheme:

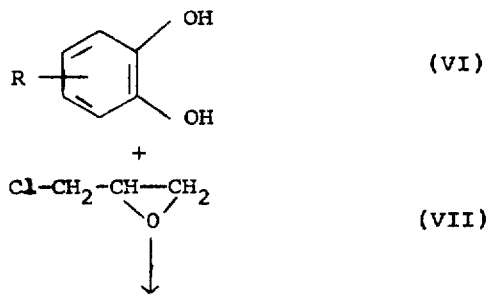

The compounds of general formula (I) and non-toxic salts thereof are useful in therapy especially as vasodilating and α-blocking agents in the treatment of cardiovascular illnesses.

The compounds of general formula (I) or salts thereof can be administered in the form of pharmaceutical compositions consisting essentially of an effective amount of at least one compound of general formula (I) or a non-toxic acid additon salt thereof, and a pharmaceutically acceptable carrier or diluent.

The following Examples illustrate the invention.

EXAMPLE 1

1-[2-(1,4-Benzodioxanyl)-methyl]-4-(2-hydroxyethyl)-piperazine dihydrochloride (comparison compound)

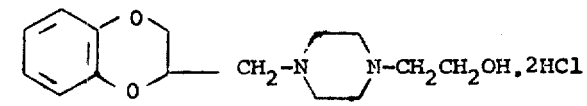

Code number LL 1756 a. 143 g (1.3 mols) of pyrocatechol, 361 g (3.9 mols) of epichlorohydrin and 500 ml of N sodium hydroxide solution are introduced into a 4 l flask equipped with a stirrer, condenser, thermometer and heating mantle.

The mixture is stirred for 1 hour without heating. It is then heated under reflux for 3 hours 30 minutes. The solution is cooled in an ice bath. It is extracted 3 times with 400 ml of diethyl ether. The ether phase is washed twice with 400 ml of N sodium hydroxide solution and then with 200 ml of water. The organic phase is dried overnight over MgSO$_4$. The MgSO$_4$ is filtered off and the ether is evaporated. 202 g (yield: 93.6%) of 2-hydroxymethyl-1,4-benzodioxan are obtained.

b. 202 g (1.21 mols) of 2-hydroxymethyl-1,4-benzodioxan are introduced into a 1 liter flask equipped with a stirrer, condenser and dropping funnel, and 288 g (2.42 mols) of thionyl chloride are run in dropwise. Violent evolution of HCl is observed. The mixture is heated under reflux until HCl ceases to be evolved, that is to say for 1 hour 30 minutes. The mixture is then distilled in vacuo after having driven off the excess thionyl chloride. 175.5 g (yield: 77.2%) of 2-chloromethyl-1,4-benzodioxan are obtained.

c. 245.5 g (1.33 mols) of 2-chloromethyl-1,4-benzodioxan, 156 g (1.2 mols) of 2-ethanol-piperazine, 200 ml of dimethylformamide and 184 g (1.33 mols) of K$_2$CO$_3$ are introduced into a 2 l Erlenmeyer flask equipped with a stirrer.

The mixture is stirred and heated at 80°C for 6 hours and at 100°C also for 6 hours. The mixture is left to cool and the precipitate is filtered off and washed with 3 times 50 ml of dimethylformamide and then removed. The filtrates are combined and the desired hydrochloride is precipitated by means of 400 ml of an 8.8 N solution of hydrogen chloride in ethanol. The precipitate of hydrochloride is filtered off and washed with ether. The precipitate is dissolved in 300 ml of distilled water, the solution is cooled in an ice bath and 250 ml of sodium hydroxide solution are run in dropwise until the pH is 11 in order to obtain the base. Since the latter is soluble in water, it is extracted with 3 times 300 ml of ether, introducing inorganic salts into the aqueous phase. The ether solution is dried over MgSO$_4$. The ether is evaporated and a clear orange oil is obtained which gradually crystallises Since the purity of the product is about 70%, the base is dissolved in a liter of refluxing ethanol. 150 ml of 12 N hydrochloric acid are run in dropwise and this solution is placed in a refrigerator for 1 hour. The solution is filtered, the precipitate is washed with ethanol and the product is dried. 1.86 g of 1-[2-(1,4-benzodioxanyl)-methyl]-4-(2-hydroxyethyl)-piperazine dihydrochloride are obtained. (Yield 44.1%).

The base is recovered again as indicated above. The base thus purified has a melting point of 62°C.

EXAMPLE 2

1-[2-(1,4-Benzodioxanyl)-methyl]-4-(2-hydroxyethyl)-piperazine hemifumarate

Code number CRL 40040

10 g of base purified according to Example 1c and 4.06 g of fumaric acid are dissolved in 150 ml of refluxing ethanol. The solution is allowed to cool slowly to ambient temperature and a heavy precipitate appears. It is filtered off and dried and 9 g of hemifumarate are obtained. (Yield 64%).

Analysis % N calculated: 8.32 hemifumarate 7.12 fumarate % N found: 8.05

EXAMPLE 3

1-[2-(1,4-Benzodioxanyl)-methyl]-4-(2,3-dihydroxypropyl)-piperazine dihydrochloride

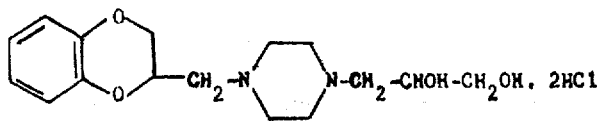

Code number CRL 40034

18.5 g of 2-chloromethyl-1,4-benzodioxan, 16.9 g of N-(2,3-dihydroxypropyl)piperazine and 30 ml of dimethylformamide are introduced into a 250 ml Erlenmeyer flask.

The mixture is heated at 80°C for 8 hours. The precipitate is filtered off, washed with DMF and removed. The hydrochloride is precipitated by pouring approximately 30 ml of a 7 N solution of hydrogen chloride in ethanol into the DMF solution. An oil forms. The DMF is decanted and ether is added in order to wash the oil formed. The ether is decanted. The residue is dissolved in the minimum amount of water. The solution is treated with sodium hydroxide solution until the pH is 11. The solution is extracted with ether and the ether phase is dried over MgSO$_4$. The aqueous phase which results from the extraction with ether is separated off and extracted with chloroform, and the chloroform phase collected is then dried over MgSO$_4$. The ether and chloroform phases are evaporated separately. In the ether phase, 5.2 g of oil are obtained [pure in thin layer chromatography, eluant CHCl$_3$ — CH$_3$OH — NH$_4$OH (40:40:20)]; in the chloroform phase, 2 g of oil are obtained (impure in thin layer chromatography).

The 5.2 g of oil resulting from the ether phase are dissolved in 100 ml of methanol and the solution is heated under reflux. During the refluxing, 10 ml of a 7 N solution of hydrogen chloride in ethanol are introduced. The mixture is cooled overnight in a refrigerator. On adding acetone, the dihydrochloride precipitates.

5.1 g (yield 13.3%) of product, which is pure in thin layer chromatography [eluant: CHCl$_3$ — CH$_3$OH — NH$_4$OH (40:40:20)], are obtained.

EXAMPLES 4 and 5

By following the procedure indicated in Example 1, and replacing pyrocatechol with 4-methyl-pyrocatechol and 4-4-(tertiary butyl)-pyrocatechol, the following products were obtained respectively:

1-[2-(6- or 7-methyl-1,4-benzodioxanyl)-methyl]-4-(2-hydroxyethyl)-piperazine dihydrochloride - code number CRL 4024 - melting at 210°C; and 1-[2-(6- or 7-(tertiary butyl)-1,4-benzodioxanyl)-methyl]-4-(2-hydroxyethyl)-piperazine dihydrochloride - code number CRL 4001 - melting at 180°C.

The uncertainty about the position of the methyl and tertiary butyl substituents of the benzodioxanyl group results from the method of preparation since it is possible for one of the following two cyclisations to take place (with R$_o$ = alkyl)

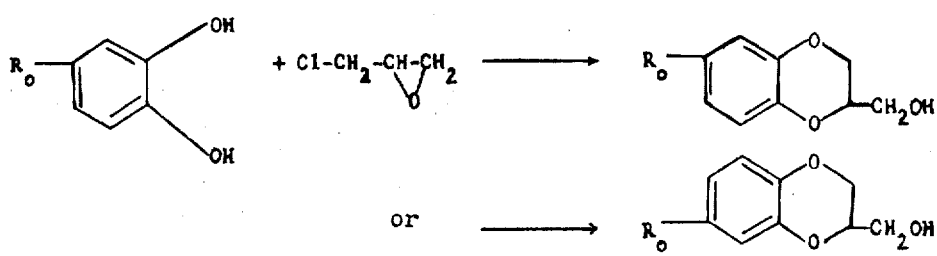

There are strong reasons to believe that derivatives substituted in the 6-position were produced.

EXAMPLE 6

1-[2-(1,4-Benzodioxanyl)-methyl]-4-[2-(propionyloxy)-ethyl]-piperazine dihydrochloride

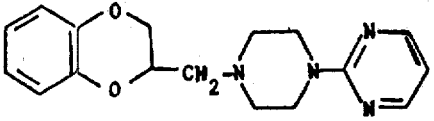

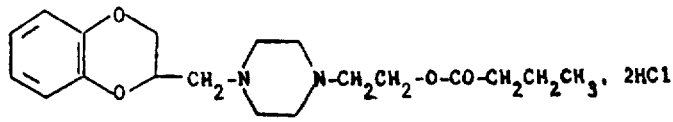

Code number CRL 4011

A mixture of 5 g (0.192 mol) of propionic anhydride and 13 g (0.037 mol) of LL 1756 (product of example 1c), which is completely soluble in hot acetic acid, is heated to the reflux temperature of acetic acid (75 ml), and refluxing is maintained for 5 hours. After having allowed the reaction mixture to cool, the acetic acid is evaporated and the residual cyrstalline residue is washed several times with ether and once with ethanol. 11.73 g (yield 77%) of dihydrochloride, which melts at 180°C, are obtained.

This product, analysed by thin layer chromatography, eluant: methanol — acetic acid (80:20), is 98% pure.

EXAMPLE 7

1-[2-(1,4-Benzodioxanyl)-methyl]-4-[2-acetyloxy)-ethyl]-piperazine dihydrochloride

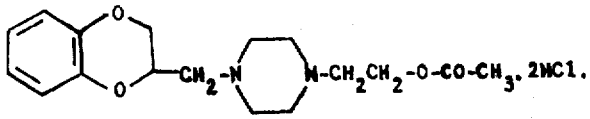

Code number CRL 4010

5 g of LL 1756 and 3 ml of acetic anhydride in 50 ml of acetic acid are heated at the boiling point for 5 hours. LL 1756 is completely soluble in hot acetic acid.

After cooling, the acetic acid is evaporated and the solid residue is washed several times with ether and then once with ethanol. The product is dried in vacuo at 50°C. 3.47 g (yield 62%) of dihydrochloride, which melts at 180°C (with decomposition), are obtained.

Analysis % of Cl, theory: 18.06% % of Cl, found: 18.31%.

EXAMPLE 8

1-[2-(1,4-Benzodioxanyl)-methyl]-4-(2-pyrimidinyl)-piperazine dihydrochloride

Code number CRL 1767

A mixture of 34.0 g (0.18 mol) of 2-chloromethyl-1,4-benzodioxan, 19.3 g (0.11 mol) of N-2-pyrimidinyl-piperazine and 25 g (0.18 mol) of $K_2CO_3$ in 30 ml of dimethylformamide is stirred for 48 hours at 100°C. The solution is filtered and the precipitate is washed with DMF. Approximately 55 ml of a 4 N solution of hydrogen chloride in ether are added in order to precipitate the product. 200 ml of ether are added and the mixture is filtered. The precipitate is washed three times with 20 ml of ether each time.

The hydrochloride is dissolved in 300 ml of water and this solution is neutralised by means of sodium hydroxide solution until the pH is 11. The base precipitates. The mixture is filtered and the precipitate obtained is washed with distilled water.

25.4 g of base are obtained. It is recrystallised from 300 ml of petroleum ether + 10 ml of acetone. Some insoluble matter in this mixture is again recrystallised from a mixture of 250 ml of petroleum ether and 50 ml of acetone.

The first recrystallization yields 5.8 g of product and the recrystallisation yields 10.5 g of product, that is to say 16.3 g in all.

The base obtained is dissolved in 200 ml of methanol and 50 ml of a 5 N solution of hydrogen chloride in ethanol are added. The dihydrochloride precipitates in the refrigerator. It is washed three times with 10 ml of ethanol each time. 17.3 g (yield 40.8%) of white dry 1-[2-(1,4-benzodioxanyl)-methyl]-4-(2-pyrimidinyl)-piperazine dihydrochloride, which melts at 160°C (melting point not instantaneous), are obtained.

EXAMPLE 9

1-[2-(1,4-Benzodioxanyl]-4-(2,6-dimethyl-acetanilido)-piperazine dihydrochloride

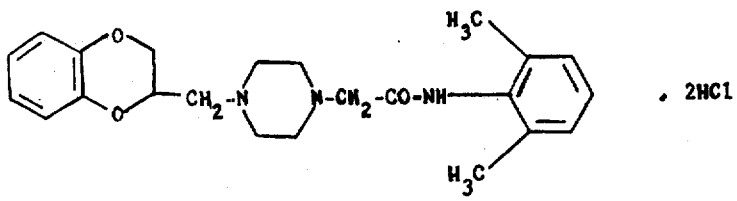

Code number CRL 40035 a. 66 g (0.6 mol) of pyrocatechol, 600 ml of N sodium hydroxide solution and 166.5 g (1.8 mols) of glycerol epichlorohydrin are mixed. The temperature of the mixture rises to 56°C. From then on, the reaction mixture is heated to the reflux temperature for 5 hours.

The mixture is extracted with 3 × 200 ml of ether. The ether solution is washed with 3 × 200 ml of N sodium hydroxide solution and 2 × 100 ml of water. It is dried over MgSO₄. The ether is evaporated. 96.6 g (yield: 96.9%) of 2-hydroxymethyl-1,4-benzodioxan crystals are obtained.

b. 44 g of 2-hydroxymethyl-1,4-benzodioxan and 100 ml of pyridine are introduced into a 250 ml three-necked flask. An orange solution is obtained. Methane sulphonyl chloride is diluted with 50 ml of pyridine (brown solution) and is run dropwise, over the course of 30 minutes, into the reaction mixture described above. At the end of the running-in process, crystals appear. Stirring is then continued for 2 hours. The mixture is filtered and the pyridine is evaporated. The crystals seem to be pyridine hydrochloride. The residual oil, present in the filtrate from which the pyridine has been removed, is taken up again in ethyl acetate and yields a new precipitate which is removed.

Evaporation of the ethyl acetate yields 64.8 g of a yellow oil which is insoluble in water (yield: 86.1%), namely 2-(1,4-benzodioxanyl)-methyl methanesulphonate.

c. 30 ml of xylene and 7 g of anhydrous piperazine are introduced into a 100 ml Erlenmeyer flask with a ground glass neck. Dissolution takes place completely on heating, without stirring. A solution of 2-(1,4-benzodioxanyl)-methyl methanesulphonate is added dropwise to the refluxing xylene; at the end of the running-in process, an oil which is insoluble in xylene is obtained. The mixture is then heated under reflux for 2 hours.

The mixture is then allowed to cool and is extracted with 2 × 20 ml of water and then with 20 ml of 4 N sulphuric acid. The phases resulting from the extraction are placed in an ice bath and are neutralised with sodium hydroxide solution. The mixture is extracted with 3 × 20 ml of ether. The solution is dried over Na₂SO₄. The solution is filtered and N-[2-(1,4-benzodioxanyl)-methyl]-piperazine dihydrochloride is precipitated by means of a solution of hydrogen chloride in ether. 3.1 g of product (yield: 50.8%) are obtained.

d. 12.83 g of chloro-2,6-dimethyl-acetanilide, 13.48 g of N-[2-(1,4-benzodioxanyl)-methyl]-piperazine dihydrochloride, 8.8 g of K₂CO₃ and 50 ml of dimethylformamide are introduced into a 250 ml Erlenmeyer flask with a ground glass neck. The mixture is stirred at ambient temperature (20°C) for 24 hours and at 80°C for 1 hour. The precipitate is filtered off, washed with dimethylformamide and removed. The filtrates are combined and 1-[2-(1,4-benzodioxanyl)-methyl]-4-(2,6-dimethylacetanilido)-piperazine dihydrochloride, in DMF, is precipitated by means of 30 ml of a 5.4 N solution of hydrogen chloride in ether. The precipitate is filtered off and drained. It is dissolved in distilled water and treated with sodium hydroxide solution until the pH is 11. The base precipitates. It is filtered off and dissolved in ether. The ether phase is dried over MgSO₄ overnight. The desired dihydrochloride is reprecipitated in a mixture of hydrogen chloride and ether. 10 g of product (yield: 28.5%) are obtained.

EXAMPLE 10

1-[2-(1,4-Benzodioxanyl)-methyl]-4-(α-carbethoxyethyl)-piperazine dihydrochloride

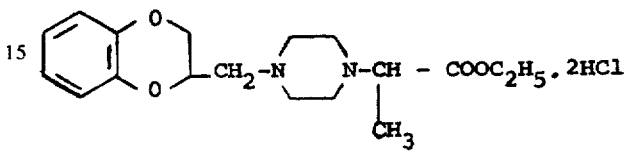

Code No. CRL 40,135

57.61 G (0.219 mol) of N-[2-(1,4-benzodioxanyl)-methyl]-piperazine, 47.60 g (0.263 mol) of ethyl α-bromopropionate, 27.90 g (0.263 mol) of anhydrous Na₂CO₃ and 200 ml of anhydrous DMF (dried over MgSO₄) are stirred for 24 hours at ambient temperature (15°–25°C). The insoluble material (Na₂CO₃ + NaBr) is filtered off and the latter is washed with DMF. The desired compound is then precipitated in DMF by adding 120 ml of 5N-hydrogen chloride in ether. The product is filtered off and washed with ether. The crude product this obtained is dissolved in water and the pH of the aqueous phase adjusted to 11.

The base of the product is extracted with chloroform (4 × 100 ml.). The solution is dried over MgSO₄, the MgSO₄ is filtered off and the chloroform is evaporated.

The residue is taken up in ether (800 ml) and the hydrochloride is precipitated by means of 100 ml of 5N-hydrogen chloride in ether. The hydrochloride is filtered off and dissolved in water, and 20 ml of concentrated hydrochloric acid are added to the aqueous solution. The water is evaporated to leave a dry product and the residue is recrystallised from absolute ethanol to give 42.2 g. (yield 47.3%) of the title compound, m.p. 154°C. Analysis: Found: Cl, 17.09%; Theoretical 17.44%.

EXAMPLE 11

1-[2-(1,4-Benzodioxanyl)-methyl]-4-[2-(3,5-dimethoxyphenoxy)-ethyl]-piperazine dihydrochloride

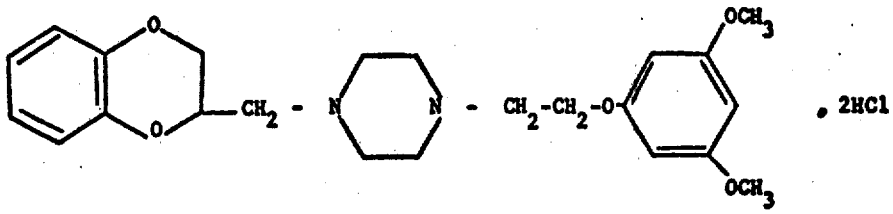

Code No. CRL 40,146

28.1 G (0.129 mol) of 1-chloro-2-(3,5-dimethoxyphenoxy)-ethane, 27.14 g (0.116 mol) of N-[2-(1,4-benzodioxanyl)-methyl]-piperazine, 17.8 g (0.129 mol) of anhydrous K₂CO₃ and 200 ml of DMF (dried over MgSO₄) are heated at 100°C, with stirring, for 3½ hours. The mixture is cooled. The insoluble material (K₂CO₃ + KCl) is filtered off and washed with DMF. The hydrochloride is precipitated in DMF with 60 ml of 5N-hydrogen chloride in ether. The hydrochloride is washed with ether.

The hydrochloride is taken up in the minimum amount of water. The pH of the aqueous phase is adjusted to 11 using sodium hydroxide solution. The base of the product is extracted with chloroform (4 × 50 ml.). The chloroform extract is dried over MgSO₄. The MgSO₄ is filtered off. The chloroform is evaporated, the residue is taken up in 200 ml of methanol and the hydrochloride is precipitated with 60 ml of 5N-hydrogen chloride in ether. The product is filtered off and recrystallised from methanol to give 24.6 g (yield 43%) of the title compound, m.p. 170°C. Analysis: Found: Cl, 14.52%; Theoretical: Cl, 14.59%.

EXAMPLE 12

1-[2-(1,4-Benzodioxanyl)-methyl]-4-[(2-hydroxy-2-phenyl)-ethyl]-piperazine dihydrochloride

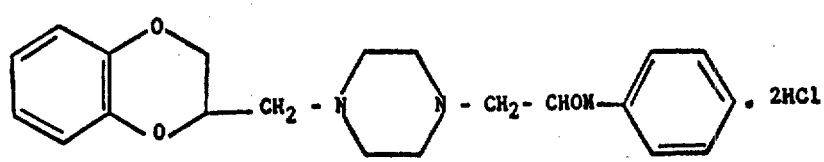

Code No. CRL 40,150

30.7 G (0.10 mol) of N-[2-(1,4-benzodioxanyl)-methyl]-piperazine dihydrochloride are dissolved in distilled water. The pH of the aqueous phase is adjusted to 11 with sodium hydroxide solution. The base is extracted with chloroform (3 × 100 ml.). The chloroform phase is dried over MgSO₄, the MgSO₄ is filtered off, the chloroform is evaporated, the residue is taken up in 215 ml of methanol/water (95:5) and 13.20 g (0.11 mol) of phenylethylene oxide are added. The mixture is then refluxed for 3 hours.

Thin layer chromatography [eluting agent: CH₃OH/CH₂Cl₂/NH₄OH (60:20:20); Merck F₂₅₄ silica gel plate; revealed by means of Draggendorf's solution] shows that the reaction is complete. The mixture is cooled and the methanol is evaporated. The residue is taken up in the minimum amount of distilled water and the pH is adjusted to 11 with sodium hydroxide solution. The base is extracted with chloroform (4 × 100 ml.). The chloroform extract is dried over MgSO₄; the chloroform is evaporated, the residue is taken up in 200 ml of methanol and the product is precipitated with 50 ml of 5N-hydrogen chloride in ether. The mixture is cooled and filtered. The hydrochloride thus obtained is dissolved in distilled water and the pH of the solution is adjusted to 11 with sodium hydroxide solution. The free base is extracted with chloroform (4 × 100 ml.).

The chloroform extract is dried over MgSO₄ and the solvent is evaporated; the residue is taken up in 200 ml of methanol and the hydrochloride is precipitated with 50 ml of 5N-hydrogen chloride in ether. Recrystallisation from methanol gives 14.25 g. (yield 33%) of the title compound, m.p. 144°C. Analysis: Found: Cl, 16.53%; Theoretical = Cl, 16.62%.

EXAMPLE 13

1-[2-(1,4-Benzodioxanyl)-methyl]-4-(2,4,6-trimethoxyphenacyl)-piperazine dihydrochloride

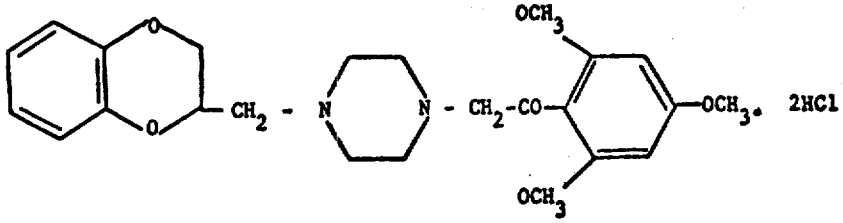

Code No. CRL 40,156

12.94 G (0.0533 mol) of N-[2-(1,4-benzodioxanyl)-methyl]-piperazine, 15 g (0.0613 mol) of 2,4,6-trimethoxychloroacetophenone, 7 g (0.0613 mol) of anhydrous Na₂CO₃ and 100 ml of anhydrous DMF are heated at 100°C for 1 hour.

Thin layer chromatography as performed in Example 12 shows that the reaction is complete.

The mixture is cooled, the insoluble material (Na₂CO₃ + NaCl) is filtered off and the hydrochloride is precipitated with 30 ml of 5N-hydrogen chloride in ether. The mixture is filtered, the hydrochloride is washed with ether and dissolved in distilled water and the pH of the aqueous phase is brought to 11 with sodium hydroxide solution. The base of the title compound is extracted with ethyl acetate (3 × 100 ml.), the extracts are dried over MgSO₄, the MgSO₄ is filtered off and the hydrochloride is precipitated with 30 ml of 5N-hydrogen chloride in ether and then filtered off. Recrystallisation from 200 ml of methanol gives 15 g (yield 52.6%) of the title compound, m.p. 174°C. Analysis: Found: Cl, 13.71%; Theoretical: Cl, 13.78%.

The products of Examples 10 to 13 are listed in Table I below.

The results of the pharmacological tests which were undertaken with the products of Examples 1 to 9 have been summarised below. These results demonstrate a vasodilating activity and an α-blocking activity of the adrenergic receptors.

The data relating to toxicity have been summarised in the Table below.

TABLE

| Example | LD-50 I.V. in mice (mg/kg) | Maximum non-toxic dose (1) (mg/kg) |
|---|---|---|
| 2 | 97 ± 2 | 90 |
| 3 | 260 ± 11 | >170 |

TABLE-continued

| Example | LD-50 I.V. in mice (mg/kg) | Maximum non-toxic dose (1) (mg/kg) |
|---------|---------------------------|-----------------------------------|
| 5 | 140 ± 8 | 100 |
| 6 | 109 ± 9 | — |
| 7 | 86 ± 1 | 80 |
| 8 | 145 ± 10 | — |

Vasodilating properties

During the series of pharmacological tests, the following parameters were used:

Arterial pressure (abbreviated to AP): this parameter, expressed in mm Hg) is evaluated in accordance with the usual conditions.

Arterial resistance: this parameter (expressed in dynes/sec./cm$^{-5}$) is calculated according to the ratio $$\text{Resistance:} \frac{\text{Average } AP \text{ (mm Hg)} \times 980 \times 1.36 \times 60}{\text{cardiac output (ml/min.)}}$$

Cardiac index: this parameter is expressed in ml/min./kg.

Systolic index: this parameter is equal to the ratio cardiac index/frequency.

Cardiac work: this parameter (expressed in kgm/min.) is calculated according to the relationship: Cardiac work = average AP (mm Hg) × 1.36 = cardiac output (l/min.) × $10^{-3}$.

Ratio dp/dt: this parameter corresponds to the variation in pressure expressed in mm Hg per second (in English: Rate of rise of left ventricular pressure).

The technique used to measure the ratio dp/dt is as follows:

The cardiac output is determined in Beagle dogs weighing 10 to 15 kg, anesthetised with pentobarbital, by injecting Cardiogreen (1 mg in 0.5 ml) into the right ventricle. A catheter introduced via the carotid artery into the aorta makes it possible to aspirate arterial blood at the rate of 25 ml/min. and to pass it in front of the photoelectric cell of a Beckman cardiodensitometer. The results are interpreted in accordance with the Hamilton method.

In the case of the product of Example 2, the vasodilating properties were investigated in dogs.

On injection into the femoral artery, no effect is observed at doses of less than 100 μg/kg. At a dose of 1 mg/kg, the flow rate of the femoral artery is increased by 34%; it increases by 90% at a dose of 10 mg/kg; it is only increased by 67% at a dose of 20 mg/kg. At these doses, no effect is observed on the arterial pressure AP measured in accordance with the usual conditions.

On injection into the vertebral artery, no effect is observed at doses of less than 1 mg/kg. At a dose of 10 mg/kg, the flow rate increases by 37% and at a dose of 20 mg/kg it only increases by 27%. At these two doses, the arterial pressure decreases respectively by 14 and 28% although no effect had been observed during the injection into the femoral artery.

When administered intravenously, the following results were observed:

In a first test, the product of Example 2, perfused intravenously at a dose of 0.25 mg/kg, increases the vertebral flow rate by 90% at the start of perfusion but only by 14% at the end of perfusion. Additional injections at doses of 0.5 and 5 mg/kg have no effect on the flow rate.

In a second test, a dose of 0.5 mg/kg is injected at the very start and it increases the vertebral flow rate by 135% at the beginning of perfusion and by 58% at the end of perfusion. Subsequent injections at doses of 1 and 2 mg/kg have no effect on the flow rate.

In both these tests, the pulse rate is increased and this effect persists during successive injections.

A third test is carried out by injecting, without stopping, 0.5, 1, 2 and 4 mg/kg, that is to say a total of 7.5 mg/kg. The flow rate of the vertebral artery increases at each of the injections up to the third, whilst the femoral flow rate, which is increased very much by the first injection, decreases during the subsequent injections. The flow rate of the mesenteric artery is uniformly decreased by 25% at each injection.

In another test, the product of Example 2, injected at a dose of 2 mg/kg at the very start, raises the flow rate of the vertebral artery by 87% for more than one hour, whilst the flow rate of the femoral artery is only increased greatly during the injection.

The product of Example 2 does not alter the effects of the injection of acetylcholine and isoprenalin nor that of the stimulation of the peripheral vagus, but it reverses the hypertensive effect of adrenalin in a lasting manner.

Furthermore, the coronary flow rate was observed in anaesthetised dogs perfused intravenously at a dose of 5 mg/kg and the following effects were noted: A hypotension of 15 to 38% which can last for more than 2 hours; an increase of 40% in the differential arterial pressure for 1 hour due to lowering of the diastolic arterial pressure; a tachycardia (+ 40%) for a period of more than 2 hours, and an increase in the cardiac work: The maximum intraventricular pressure increases (+ 56%) for 1 hour, the ratio dp/dt increases(+ 180%) for more than 1 hour and the ejection time decreases (25 to 30%); a great increase in the coronary flow rate with the maximum effect (+ 200%) being shown after 1 hour, whilst 2 hours after the injection the flow rate is still increased by 75%.

To summarise, the product of Example 2 acts as an α-lytic product, which can dilate either the vertebral artery or the femoral artery or both. Moreover, it possesses tachycardiac properties at low doses; at a higher dose, it is hypotensive. It increases the cardiac work and, in parallel fashion, it increases the coronary irrigation.

In animal pharmacology, the active doses are approximately 1/100th and even 1/200th of the LD 50 I.V. in mice.

In clinical studies, good results were obtained in man by administering tablets such as:

1-[2-(1,4-Benzodioxanyl)-methyl]-4-
(2-hydroxyethyl)-piperazine hemifumarate    50 mg
Excipient, q.s.p.    500 mg to 1,000 mg
or injectable ampoules such as:
1-[2-(1,4-Benzodioxanyl)-methyl]-4-
(2-hydroxyethyl)-piperazine hemifumarate    10 mg
NaCl solution, of concentration 9 g/l, q.s.p. 3 ml ampoule.

The product of Example 8 was investigated in dogs anaesthetised by means of Nembutal. The product of Example 8 was perfused intravenously over the course of 5 minutes at doses of 2.5 and 5 mg/kg. At a dose of 2.5 mg/kg, an increase in the differential arterial pressure (+ 50%), a tachycardia (+ 19%), a slight femoral vasodilating effect (+ 19%) and a decrease in the vertebral flow rate (19%), and practically no effect on the mesenteric flow rate, are observed.

With the product of Example 8, the hypertensive effect of adrenalin is reversed, and this manifests itself in an α-blocking action.

When administered orally, the product of Example 8 does not alter the flow rate of the femoral artery; nor that of the vertebral artery, at doses of less than 100 μg/kg. At higher doses, that is to say of 1 to 10 mg/kg (at a dose of 10 mg/kg the product passes into the general circulation), a rise in the flow rates is noted: + 200% in the case of the femoral flow rate and + 60% in the case of the vertebral flow rate for 30 minutes.

Cardiovascular properties of the product of Example 3

When administered intravenously to dogs at doses ranging from 1 mg to 13 mg/kg, the following results are observed:

An increase in the differential AP, little effect on the AP or a slight hypotension, a rise in the pulse rate which does not exceed 25%, an increase in dp/dt with a shortening of the ejection time, the cardiac output is scarcely changed, and no effect on the vertebral flow rate;

when administered intraduodenally, the product passes easily through the intestinal barrier; at doses of 10 and 50 mg/kg administered intraduodenally, the variations described after intravenous injection are found again. A dose of 10 mg/kg administered intraduodenally leads to a reversal of the hypertensive effect of adrenalin.

In conclusion, the product of Example 3 is an α-blocking agent which passes through the intestinal barrier.

When administered to man in the form of tablets containing 20 mg, (at the rate of) 2 to 3 per day, it gave good results in vascular complaints.

Vasodilating properties of the product of Example 5

Local administration: When injected locally into the femoral artery or into the vertebral artery of dogs, the product increases both these flow rates in proportion to the doses, but with a preference for the femoral flow rate.

General administration:

Intravenous administration:

2 dogs received the product of Example 5 successively at doses of 3.75 and 15 mm/kg, by intravenous administration. The following results are observed:

A femoral vasodilating action for 10 to 15 minutes, not proportional to the dose, maximum (+ 60%) from 3.5 mg/kg;

no vertebral dilating action;

no effect on the AP up to 15 mg/kg; and a bradycardia at this last dose.

When administered intraduodenally, no vasodilating effect is observed in dogs receiving successively 3.5, 7, 15 and 35 mg/kg whilst the pulse rate decreases from 7 mg/kg.

To summarise, the product of Example 5 exerts an exclusively peripheral and very moderate vasodilating effect. It also possesses an analgesic activity of the morphine type when it is injected subcutaneously.

Vasodilating properties of the product of Example 6

In the case of intravenous administration, the tests were carried out on 4 anaesthetised dogs. The product is perfused intravenously over the course of 5 minutes at doses of 2.5, 5 and 10 mg/kg and, in one test, is administered intraduodenally at a dose of 10 mg/kg. A hypotensive effect proportional to the dose is observed. The pulse rate either is not altered (2 tests) or is increased. The intraventricular pressure is decreased as is the ratio dp/dt. The femoral flow rate is increased in the tests wherein an increase in the pulse rate is observed and this effect disappears in 15 minutes.

The vertebral flow rate only increases in one of the two tests wherein the pulse rate was increased.

The product is α-blocking from a dose of 5 mg/kg administered intravenously.

When administered intra-arterially, the product of Example 6 is injected directly into the femoral artery. The flow rate is increased by 200% from a dose of 10 μg. Higher doses up to and including 10 mg do not produce a greater vasodilation.

In conclusion, the product of Example 6 is an α-blocking product from a dose of 5 mg/kg administered intravenously. When it increases the femoral flow rate, this effect is of short duration and is not reproducible. The product passes through the intestinal barrier and the activity is found again at 10 mg/kg administered intraduodenally. The vasodilating effect produced by a femoral intra-arterial injection is maximal from the very start and cannot be increased by higher doses. The mechanism of the vasodilating effect thus seems to be exclusively an alphalytic mechanism.

Cardiovascular action of the product of Example 7 in anaesthetised dogs

The adrenolytic action was investigated and demonstrated in dogs from a dose of 2.5 mg/kg administered intravenously (reversal of the hypertension due to adrenalin). From this dose, a hypotension and a decrease in the left ventricular pressure, in the ratio dp/dt and in the systolic ejection time are noted, and this applies in the case of both dogs. The pulse rate does not vary markedly.

In conclusion, it is apparent from these tests that the product of Example 7 is α-lytic.

Furthermore, the dihydrochloride of Example 1 (LL 1756) and the corresponding free base described by TOLDY and colleagues were compared with the products of the invention.

On a pharmacodynamic plane, when the said free base is administered orally to dogs it does not show any α-blocking activity since it does not make it possible to counteract the hypertensive effects of adrenalin, as is the case of the products of the invention and particularly of the product of Example 2, the hemifumarate, which decreases the said effects at a dose of 5 mg/kg, inhibits them strongly at a dose of 7 mg/kg and overcomes the α + effect of adrenalin at a dose of 10 mg/kg.

LL 1756 is also α-blocking when administered parenterally, but in clinical tests, LL 1756 and the corresponding free base, both of which are soluble in water, caused vertigo in the majority of cases, whilst the products of the invention did not give rise to any vertigo.

The results of toxicological and pharmacological experiments carried out on animals using the products of Examples 10 to 13 are summarised below.

The LD$_{50}$ values for intravenous administration to mice are given in Table II below.

The compounds of the invention are α-blocking agents with respect to adrenergic receptors. The product (CRL 40,146) of Example 11 inhibits and then reverses the tension effects of adrenalin from a dose of 0.37 mg/kg upwards, administered intravenously (i.e. from 1/160th of the LD$_{50}$ upwards, administered intravenously to mice). After each injection, the product (CRL 40,150) of Example 12 gradually reduces the hypertensive effect of adrenalin and reverses the tension effects of the latter, as indicated below, relative to the animal taken itself as a control:

| | | |
|---|---|---|
| adrenalin | → | (hypertension) + 152% |
| after 0.5 mg/kg of CRL 40,150, administered intravenously | → | (hypertension) + 67% |
| after 1 mg/kg of CRL 40,150, administered intravenously | → | (hypertension) + 36% |
| after 2 mg/kg of CRL 40,150, administered intravenously | → | (hypertension) + 43% |
| after 4 mg/kg of CRL 40,150, administered intravenously | → | (hypotension) − 7% | the doses of CRL 40,150 from 0.5 to 4 mg/kg being administered successively.

Similar experiments were carried out using the product (CRL 40,156) of Example 13 in which adrenalin is injected after each dose of the product (0.1 — 0.2 — 0.4 — 1.5 — 3 — 6 mg/kg of CRL 40,156, administered intravenously). From a dose of 0.1 mg/kg upwards, the hypertensive effect of adrenalin is reduced. The hypotensive effect appears very rapidly [generally from a dose of 0.2 mg/kg (administered intravenously) upwards, this value being the average of three different experiments].

In Table III below, the effects of the products on the amines and the reflexes have been summarised.

In addition to this α-blocking effect, the products of the invention possess a hypotensive effect as demonstrated in dogs anaesthetised with Nembutal; the hypotension is 40%, 37% and 39 to 42% (depending on the experiments) for the products of Examples 11, 12 and 13 respectively. This hypotension manifests itself especially in a decrease in the differential pressure, the lowering of the diastolic pressure being greater than that of the systolic pressure.

A vasodilating effect is also observed, especially when the products are administered intra-arterially (into the femoral artery).

Complementary experiments carried out on anaesthetised dogs have been given below for the product of Example 11 administered intraduodenally (ID).

The product was investigated by intraduodenal administration to dogs anaesthetised with Nembutal, in four experiments, A B C and D.

Experiment A (0, 14.8 kg)

Two intraduodenal administrations of 15 and 30 mg/kg of the product have no effect on the vertebral flow rate and the femoral flow rate, the starting values of which are respectively, 35 and 52 ml/minute. The arterial pressure is not altered. The pulse rate increases by at most 20% after 15 minutes and then decreases slowly (+ 14% after 30 minutes).

The tension effects of adrenalin are reversed 5 minutes after the first dose and prove that the product has passed through the intestinal barrier.

Experiment B (0, 12.8 kg)

During this experiment, the product proves to be active and raises the femoral flow rate by 134%, 5 minutes after the intraduodenal administration of 15 mg/kg (+ 194%, 15 minutes afterwards). After 1 hour, the femoral flow rate has still been increased by 100% (from 36 to 72 ml/minute). A second administration of 30 mg/kg does not change the flow rate further for the first 45 minutes, but, after 1 hour, the latter reaches 104 ml/minute (+ 184%) and, after 2 hours, it is 92 ml/minute (+ 156%).

The third administration, at the same dose as the above preceding one (30 mg/kg, administered intraduoenally), gradually increases the femoral flow rate to 108 ml/minute (+ 200%).

The average arterial pressure decreases by 18% at most (165 to 135 mm Hg).

The differential arterial pressure increases by 30%.

The increase in the pulse rate (which can be as much as 30%) is generally at a maximum 5 to 10 minutes after administration of the product.

Experiment C (0, 16 kg)

This experiment is carried out after administration of the product. The α-receptors of the animal are already blocked. The reference femoral flow rate is high (72 ml/minute). The vertebral flow rate is 20 ml/minute.

It is found that injections of adrenalin carried out after administration of the product (that is to say after blocking of the α-receptors) demonstrate the β-stimulating effect of this amine which manifests itself by an increase (of greater or lesser magnitude and of greater or lesser duration) in the femoral flow rate and even in the vertebral flow rate. The following experiment is performed in order to verify these findings:

| | |
|---|---|
| 14¾ hr.: | The product is administered intraduodenally at a dose of 15 mg/kg (a single injection). The effect of the product on the femoral flow rate is zero. The vertebral flow rate increases from 20 to 27 ml/minute (+ 35%) after 60 minutes. |
| 15 hr. 5 min: | Adrenalin: 2 mcg/kg administered intravenously; 2 minutes after the injection, the vertebral flow rate is 60 ml/minute (+ 200%). The femoral flow rate does not change. After 5 minutes, the vertebral flow rate changes to 68 ml/minute (+ 24%) and the femoral flow rate to 108 ml/minute (+ 50%). After 10 minutes, the flow rates have increased by 80% (vertebral) and 39% (femoral). |
| 15 hr. 20 min.: | Adrenalin: 10 mcg/kg administered intraduodenally. When administered in this way, this amine again increases the vertebral flow rate by 190% and the |

-continued

| | |
|---|---|
| 16 hr. 3 min.: | Adrenalin: 10 mcg/kg administered intraduodenally. Both flow rates rise again; 10 minutes afterwards, the vertebral flow rate reaches 64 ml/minute (+ 220%) and the femoral flow rate reaches 125 ml/minute (+ 73%). |
| 16 hr. 23 min. | Propanolol: 0.3 mg/kg administered intravenously. The vertebral flow rate and the femoral flow rate stabilise at their control value, which demonstrates that the effects observed are due to activation of the β-receptors. |
| Experiment D (0, 14.5 kg) | |
| 12 hr.: | Administration of the product, 15 mg/kg being administered intraduodenally. The vertebral flow rate does not change much and increases by 16% at most, whilst the femoral flow rate changes from 48 to 130 ml/minute (+ 170%) 10 minutes after administration of the product. After 30 minutes, the increase in the femoral flow rate is still 100% (50%, 75 minutes afterwards). The arterial pressure increases by approximately 10%. The systolic pressure is decreased by 8 to 30%, which manifests itself in a large increase in the differential pressure, the average pressure remaining constant. The pulse rate increases by 20 to 33%. Injections of isoprenalin and adrenalin, administered intravenously and intraduodenally, do not cause substantial changes in the graph. |
| 14 hours 35 minutes | Administration of the product, 15 mg/kg being administered intraduodenally. A second injection of the product significantly increases the vertebral flow rate, which reaches 70 ml/minute (+ 94% after 15 minutes). The femoral flow rate is increased by only 25%. | femoral flow rate by 56% after 15 minutes. After 40 minutes, the increase is 120% (vertebral flow rate) and 50% (femoral flow rate).

TABLE I

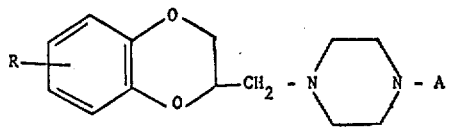

| Example | R | A | Melting point, °C | Code No. |
|---|---|---|---|---|
| 10 | H | CH(CH$_3$)COOC$_2$H$_5$ | 154°C (a) | CRL 40,135 (a) |
| 11 | H | CH$_2$CH$_2$O-(2,5-dimethoxyphenyl) | 170°C (b) | CRL 40,146 (b) |
| 12 | H | CH$_2$CHOH—C$_6$H$_5$ | 144°C (b) | CRL 40,150 (b) |
| 13 | H | CH$_2$CO-(2,4,5-trimethoxyphenyl) | 174°C (b) | CRL 40,156 (b) |

Notes:
(a) hemifumarate,
(b) dihydrochloride.

TABLE II

| Example | Code No. | LD$_{50}$, i.v., mice |
|---|---|---|
| 11 | CRL 40,146 | 60 mg/kg (a) |
| 12 | CRL 40,150 | 40 mg/kg (a) |
| 13 | CRL 40,156 | 58 mg/kg (b) |

Notes:
(a) determined on a group of male and female mice.
(b) determined on a group consisting solely of female mice.

TABLE III

| Effect on the amines and reflexes | Example 11 CRL 40,146 | Example 12 CRL 40,150 | Example 13 CRL 40,156 |
|---|---|---|---|
| adrenalin | reversal | reversal | reversal |
| acetylcholine | no change | no change | no change |
| DMPP | effect much reduced or reversed | effect much reduced or reversed | effect reversed |
| stimulation of the peripheral vagus | not changed | reduced in one experiment out of two | not changed |
| stimulation of the central vagus | not changed | reduced in one experiment out of two | slightly reduced |
| reflex relating to occlusion of the carotids | reduced | unchanged | blocking of the hypertensive effect |

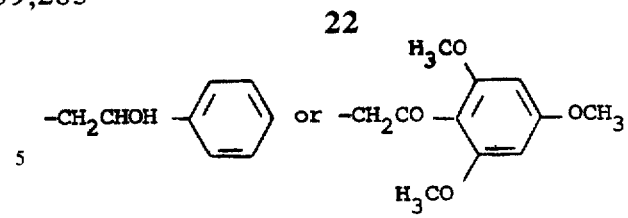

or a non-toxic acid addition salt thereof.

I claim:
1. A compound of formula:

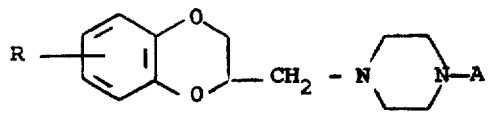

in which R is hydrogen or alkyl of 1 to 5 carbon atoms; and A is —CH(CH$_3$)COOC$_2$H$_5$,

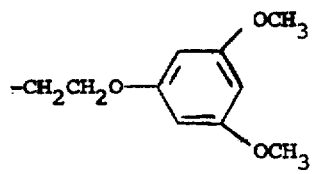

2. A compound as claimed in claim 1 which is 1-[2-(1,4-benzodioxanyl)-methyl]-4-(α-carbethoxy-ethyl)-piperazine or a non-toxic addition salt thereof.

3. A compound as claimed in claim 1 which is 1-[2-(1,4-benzodioxanyl)-methyl]-4-[2-(3,5-dimethoxyphenoxy)-ethyl]-piperazine or a non-toxic addition salt thereof.

4. A compound as claimed in claim 1 which is 1-[2-(1,4-benzodioxanyl)-methyl]-4-[(2-hydroxy-2-phenyl)-ethyl]-piperazine or a non-toxic acid addition salt thereof.

5. A compound as claimed in claim 1 which is 1-[2-(1,4-benzodioxanyl)-methyl]-4-(2,4,6-trimethoxyphenacyl)-piperazine or a non-toxic acid addition salt thereof.

6. A pharmaceutical composition consisting essentially of an effective amount of at least one compound as claimed in claim 1, or a non-toxic acid addition salt thereof, and a pharamceutically acceptable carrier or diluent.

* * * * *